United States Patent
Gunawardana

(10) Patent No.: US 9,669,128 B2
(45) Date of Patent: Jun. 6, 2017

(54) PROCESS FOR PRODUCING TIO₂ BASED PHOTOCATALYTIC COATING, THE TIO₂ PHOTOCATALYTIC COATING OBTAINED BY THE PROCESS, AND ARTICLES WITH TIO₂ BASED PHOTOCATALYTIC COATING APPLIED THEREON

(71) Applicant: ROSARIO COSMETICS PVT. LTD., Haryana (IN)

(72) Inventor: Manju Gunawardana, Kottawa (LK)

(73) Assignee: ROSARIO COSMETICS PVT. LTD., Gurgaon, Haryana (IN)

( * ) Notice: Subject to any disclaimer, the term of this patent is extended or adjusted under 35 U.S.C. 154(b) by 0 days.

(21) Appl. No.: 14/648,262

(22) PCT Filed: Jan. 27, 2014

(86) PCT No.: PCT/IB2014/058571
§ 371 (c)(1),
(2) Date: May 29, 2015

(87) PCT Pub. No.: WO2014/115119
PCT Pub. Date: Jul. 31, 2014

(65) Prior Publication Data
US 2015/0306270 A1    Oct. 29, 2015

(30) Foreign Application Priority Data
Jan. 28, 2013   (IN) ............................. 202/DEL/2013

(51) Int. Cl.
B32B 15/04     (2006.01)
G03C 1/00     (2006.01)
(Continued)

(52) U.S. Cl.
CPC ............... *A61L 9/18* (2013.01); *B01J 21/063* (2013.01); *B01J 23/06* (2013.01); *B01J 23/10* (2013.01);
(Continued)

(58) Field of Classification Search
CPC . B05D 3/02; A61L 2/0076; C09D 5/32; C08F 220/14
(Continued)

(56) References Cited

U.S. PATENT DOCUMENTS

2005/0191505 A1   9/2005   Akarsu et al.
2007/0172662 A1*   7/2007   Ferencz ................. C09D 5/032
                                                                                           428/411.1
(Continued)

FOREIGN PATENT DOCUMENTS

| CN | 102199004 A | 9/2011 |
|---|---|---|
| EP | 2300548 A4 | 6/2012 |
| JP | 2000303027 A | 10/2000 |

OTHER PUBLICATIONS

The Search Report from International Application No. PCT/IB2014/058571 issued on May 27, 2014.

*Primary Examiner* — Monzer R Chorbaji
(74) *Attorney, Agent, or Firm* — United IP Counselors, LLC

(57) ABSTRACT

A water soluble photocatalytic material capable of being adhered to an article by a conventional coating process is described. The photocatalytic material includes a doped metal oxide substrate capable of exhibiting photocatalytic behavior on being exposed to visible light, wherein particle size of doped metal oxide substrate ranges from about 18 nanometer (nm) to about 35 nm. Further, the photocatalytic material includes a polymeric adhesive for improving the adhering property of the doped metal oxide substrate on the article. In addition, a process for producing the water soluble
(Continued)

EFFECT OF CLF COATED LAMP IN THE REDUCTION OF VARIOUS MICROBIAL CULTURES

First Test:

| Sr. No. | Test Parameter | Specified Requirement Incubation Time/ Temperature | Test Results After Exposure (6 Hours) | After Exposure (12 Hours) | After Exposure (24 Hours) |
|---|---|---|---|---|---|
| 1. | Escherichia Coli Germ Kill Efficiency (%) | 35-37°C for 24 hrs | 46% | 82% | 95% |
| 2. | Staphylococcus Aureus Germ Kill Efficiency (%) | 35-37°C for 24 hrs | 35% | 81% | 93% |
| 3. | Salmonella Typhi Germ Kill Efficiency (%) | 35-37°C for 24 hrs | 52% | 79% | 95% |
| 4. | Streptococcus Germ Kill Efficiency (%) | 35-37°C for 24 hrs | 56% | 80% | 92% |

Second Test:

| Sr. No. | Test Parameter | Media - Used | Specified Requirement Incubation time/Temp | Before Exposure | Test Results After Exposure (6 Hours) | After Exposure (12 Hours) | After Exposure (24 Hours) |
|---|---|---|---|---|---|---|---|
| 1. | Total Bacterial Count | NA (Nutrient Agar) | 37°C for 24 hrs | 17 | 7 cfu | 2 cfu | Nil |
| | Germ Kill Efficiency (%) | | | | 59% | 88% | 94% |
| 2. | Total Fungal Count | PDA (Potato Dextrose Agar) | 25°C for 120 hrs | 5 | 3 cfu | 1 cfu | 1 cfu |
| | Germ Kill Efficiency (%) | | | | 40% | 80% | 80% |

Third Test:

| Sr. No. | Test Parameter | Incubation time/Temp | After Exposure (6 Hours) | After Exposure (12 Hours) | After Exposure (24 Hours) |
|---|---|---|---|---|---|
| 1 | Campylobacter Germ Kill Efficiency (%) | 42°C for 48 hrs | 98.1% | 99.1% | 100% | photocatalytic material is described. Further, an air purifying article, such as a sheet, on which the said photocatalytic material is applied to is also described.

23 Claims, 5 Drawing Sheets

(51) Int. Cl.
*A61L 9/18* (2006.01)
*B01J 35/00* (2006.01)
*C09J 133/04* (2006.01)
*B01J 21/06* (2006.01)
*B01J 23/42* (2006.01)
*B01J 23/50* (2006.01)
*B01J 23/80* (2006.01)
*B01J 27/24* (2006.01)
*B01J 23/06* (2006.01)
*B01J 23/10* (2006.01)
*B01J 31/06* (2006.01)
*B01J 31/38* (2006.01)
*B01J 35/02* (2006.01)
*C08K 3/22* (2006.01)
*C08K 9/02* (2006.01)

(52) U.S. Cl.
CPC ............... *B01J 23/42* (2013.01); *B01J 23/50* (2013.01); *B01J 23/80* (2013.01); *B01J 27/24* (2013.01); *B01J 31/06* (2013.01); *B01J 31/38* (2013.01); *B01J 35/004* (2013.01); *B01J 35/0006* (2013.01); *B01J 35/023* (2013.01); *C09J 133/04* (2013.01); *C08K 9/02* (2013.01); *C08K 2003/2241* (2013.01); *C08K 2201/005* (2013.01)

(58) Field of Classification Search
USPC .............................. 422/24; 428/469; 252/600
See application file for complete search history.

(56) References Cited

U.S. PATENT DOCUMENTS

2009/0136405 A1   5/2009   Matsui et al.
2010/0304059 A1   12/2010  Besson et al.

\* cited by examiner d = Tio2 with 4% platinum Doped 48 Hours stirred and Stabilized
e = Tio2 with 4% platinum doped 24 Hours stirred and Stabilized
g = Tio2 with 2% platinum doped 24 Hours stirred and Stabilized
h = Tio2 with 2% platinum doped 48 Hours stirred and Stabilized

Chemical Parameters:

| Sr. No. | Parameters | Units | A:13:02:0042 | Specified Limits |
|---|---|---|---|---|
| 1 | Respirable Suspended Particulate Matter PM-10 | $\mu g/m^3$ | 554.9 | 100 |
| 2 | Respirable Suspended Particulate Matter PM-2.5 | $\mu g/m^3$ | 391.8 | 60 |
| 3 | Temperature | °C | 27.2 | <25.5 |
| 4 | Relative Humidity | % | 75 | <70 |
| 5 | Carbon Dioxide | % | 0.03 | <1 |
| 6 | Carbon Monoxide | ppm | Not detected | <35 |
| 7 | Oxygen | % | 20.9 | >19.5 |
| 8 | Ozone | ppm | Not detected | <0.1 |
| 9 | Nitrogen Dioxide | ppm | Not detected | <1 |
| 10 | Sulphur Dioxide | ppm | Not detected | <2 |
| 11 | Total Volatile Organic Compounds | ppm | Not detected | <500 |
| 12 | Hydrogen Sulphide | ppm | Not detected | <10 |
| 13 | Ammonia | ppm | Not detected | <50 |
| 14 | Formaldehyde | ppm | Not detected | <1 |

FIG. 2

Microbiological Parameters:

| Sr. No. | Parameters | Units | A:13:02:0042 | Specified Limits |
|---|---|---|---|---|
| 1 | Total Plate Count | Cfu/min | Nil | <1,000 |
| 2 | Yeast | Cfu/min | Absent | Not specified |
| 3 | Mold | Cfu/min | Absent | Not specified |

FIG. 3

EFFECT OF CLF COATED LAMP IN THE REDUCTION OF VARIOUS MICROBIAL CULTURES

First Test:

| Sr. No. | Test | Specified Requirement | Test Results | | |
|---|---|---|---|---|---|
| Sr. No. | Parameter | Incubation Time/ Temperature | After Exposure (6 Hours) | After Exposure (12 Hours) | After Exposure (24 Hours) |
| 1. | *Escherichia Coli* Germ Kill Efficiency (%) | 35-37°C for 24 hrs | 48% | 82% | 95% |
| 2. | *Staphylococcus Aureus* Germ Kill Efficiency (%) | 35-37°C for 24 hrs | 35% | 81% | 93% |
| 3. | *Salmonella Typhi* Germ Kill Efficiency (%) | 35-37°C for 24 hrs | 52% | 79% | 95% |
| 4. | *Streptococcus* Germ Kill Efficiency (%) | 35-37°C for 24 hrs | 56% | 80% | 92% |

Second Test:

| Sr. No. | Test | Specified Requirement | | | Test Results | | |
|---|---|---|---|---|---|---|---|
| Sr. No. | Parameter | Media - Used | Incubation time/Temp | Before Exposure | After Exposure (6 Hours) | After Exposure (12 Hours) | After Exposure (24 Hours) |
| 1. | *Total Bacterial Count* | NA (Nutrient Agar) | 37°C for 24 hrs | 17 | 7 cfu | 2 cfu | Nil |
|  | Germ Kill Efficiency (%) |  |  |  | 59% | 88% | 94% |
| 2. | *Total Fungal Count* | PDA (Potato Dextrose Agar) | 25°C for 120 hrs | 5 | 3 cfu | 1 cfu | 1 cfu |
|  | Germ Kill Efficiency (%) |  |  |  | 40% | 80% | 80% |

Third Test:

| Sr. No. | Test | Specified Requirement | Test Results | | |
|---|---|---|---|---|---|
| Sr. No. | Parameter | Incubation time/ Temp | After Exposure (6 Hours) | After Exposure (12 Hours) | After Exposure (24 Hours) |
| 1 | *Campylobacter* Germ Kill Efficiency (%) | 42°C for 48 hrs | 98.1% | 99.1% | 100% |

FIG. 4

| S. no. | Area Under test | CFU Count before (11/11/2013) | CFU Count after 20h (10:30 Am 13/11/2013) | CFU count after 23h (1:30pm 13/11/2013) | CFU count after 26h (4:30pm 13/11/2013) | CFU count after 44h (10:30am 14/11/2013) |
|---|---|---|---|---|---|---|
| I. BUS | | | | | | |
| 1. | Front glass | 42 | 1 | No growth | No growth | No growth |
| 2. | Head rest | 18 | 7 | 3 | No growth | 1 |
| 3. | Rear window | uncountable (TMTC) | No growth | 1 | No growth | 2 |
| 4. | Door handle | 6 | 1 | 1 | 1 | 1 |
| 5. | Air culture | Uncountable (TMTC) | 39 | 10 | 8 | 9 |
| II. VAN | | | | | | |
| 1. | Front glass | 33 | No growth | 1 | No growth | No growth |
| 2. | Head rest | 8 | 10 | 6 | 4 | No growth |
| 3. | Rear window | 26 | No growth | 32 | 2 | No growth |
| 4. | Door handle | Uncountable (TMTC) | 8 | 18 | No growth | 1 |
| 5. | Air culture | Uncountable (TMTC) | 25 | 55 | 18 | 10 |
| III. ERTIGA | | | | | | |
| 1. | Front glass | 2 | 1 | 1 | No growth | 3 |
| 2. | Head rest | 2 | 1 | 1 | 1 | No growth |
| 3. | Rear window | 3 | No growth | No growth | 1 | 1 |
| 4. | Door handle | 2 | 4 | 3 | 2 | 1 |
| 5. | Air culture | 37 | 13 | 16 | 3 | Vehicle not available |
| IV. SHIFT VAN | | | | | | |
| 1. | Front glass | 15 | Vehicle not available | Vehicle not available | No growth | Vehicle not available |
| 2. | Head rest | 8 | - | - | No growth | Vehicle not available |
| 3. | Rear window | 5 | --- | --- | 2 | Vehicle not available |
| 4. | Door handle | 35 | --- | --- | 6 | Vehicle not available |
| 5. | Air culture | Uncountable (TMTC) | --- | --- | 20 | Vehicle not available |

FIG. 6

PROCESS FOR PRODUCING TIO₂ BASED PHOTOCATALYTIC COATING, THE TIO₂ PHOTOCATALYTIC COATING OBTAINED BY THE PROCESS, AND ARTICLES WITH TIO₂ BASED PHOTOCATALYTIC COATING APPLIED THEREON

FIELD OF THE INVENTION

The present invention relates to photocatalytic materials, and, more particularly, to a novel composition of photocatalytic material, process for producing the novel photocatalytic material, and various articles on which the photocatalytic material are applied.

BACKGROUND OF THE INVENTION

Photoreactions refer to chemical reactions induced by light. One type of photoreaction is photocatalysis. In a typical photocatalytic process, light is absorbed by an adsorbed substrate to create electron-hole pairs, which generate free radicals (e.g. hydroxyl radicals: *OH) along with oxygen. These free radicals are able to undergo very useful secondary reactions. For example, the free radicals are able to react with organic contaminants to decompose them. Therefore, such a reaction has an ability to clean air, wherein offensive, odourus, harmful gases, or the like, are decomposed to harmless forms leading to a reduction in the quantity of these unwanted elements in the surroundings.

Various materials have been used for photocatalytic process. One such material is titanium dioxide ($TiO_2$). Usually, $TiO_2$ absorbs Ultraviolet (UV)* radiation from sunlight or illuminated light source (fluorescent lamps), thereby producing electrons and holes. The electron of the valence band of titanium dioxide becomes excited when illuminated by light.

The excess energy of this excited electron promotes the electron to the conduction band of titanium dioxide therefore creating the negative-electron (e−) and positive-hole (h+) pair. The photocatalytic oxidation of an organic species often proceeds via adsorption of the pollutant on the surface of the catalyst, followed by direct subtraction of the pollutant's electrons by positively charged holes. Another possible way is oxidation with OH radicals, generated from water of the aqueous environment, which takes place at the catalyst surface or in its vicinity. Both reactions may proceed simultaneously and which mechanism dominates depends on the chemical and adsorption properties of the pollutant. Therefore, it will be appreciated that there is a reasonable need to improve the photocatalysis process so as to provide means to clean pollutants from ambient air.

Various ways are known for improving the utility of the photocatalysis process. For example, the utility of the process could be increased by developing new and better photocatalytic materials, which have better rates of cleaning the pollutants. Another way of improving the utility of the process is by developing new techniques by which better quality photocatalytic materials can be derived at a cheaper rate. Yet another way includes finding out efficient ways of increasing the practicability of such a process so as to make it easily available commercially.

Therefore, there is a continuous need for improving the photocatalysis process for variety of applications. More particularly, there is a need of water soluble photocatalytic materials, making them easily applicable on various articles by conventional process. Further, there is a need of having photocatalytic materials that have high rate of de-odourizing and purifying its surroundings.

Furthermore, there is a need of having photocatalytic materials capable of absorbing the ultra violet light from the visible light spectrum, thereby neutralizing the bad effects of ultra violet light. Additionally, there is a need of having photocatalytic materials which are easy to obtain, durable and inexpensive to manufacture.

Moreover, there is a need for manufacturing articles by applying photocatalytic materials which can be easily used by mankind and such articles with photocatalytic materials coated on them may act as a good absorbent of ultra violet light from the visible light spectrum, cleaning ambient air without degrading the luminance of light.

More specifically, there is a need for manufacturing portable articles which have photocatalytic activity, and can be easily placed at corners of various enclosed places, such as rooms, cars, and the like, for purifying the ambient air in these enclosed spaces. Such effect is supposed to bring significant advantages to the health of humans and other mammals breathing in these enclosed spaces.

SUMMARY OF THE INVENTION

Based on the needs as cited above, the present invention discloses a water soluble photocatalytic material capable of being adhered to an article, a process for producing the photocatalytic material. Further, the present invention discloses various articles with the photocatalytic material being applied thereon.

In one aspect, the invention relates to a water soluble photocatalytic material capable of being adhered to an article by a conventional coating process. The photocatalytic material includes a doped metal oxide substrate capable of exhibiting photocatalytic behavior on being exposed to visible light, wherein particle size of doped metal oxide substrate ranges from about 18 nanometer (nm) to about 35 nm. In one embodiment, the doped metal oxide substrate is doped $TiO_2$ substrate. In one embodiment, the $TiO_2$ substrate is in its anatase phase. Further, the photocatalytic material includes a polymeric adhesive for improving the adhering property of the doped metal oxide substrate on the article. In one embodiment, the polymeric adhesive is in liquid state and is an acrylic copolymer based adhesive.

In another aspect, an air purifying article has been disclosed which includes a base element and a photocatalytic material applied to the base element. The photocatalytic material has a doped metal oxide substrate capable of exhibiting photo catalytic behavior on being exposed to visible light, wherein particle size of doped metal oxide substrate ranges from about 18 nanometer (nm) to about 35 nm. In one embodiment, the doped metal oxide substrate is doped $TiO_2$ substrate. Further, the photocatalytic material includes a polymeric adhesive for improving the adhering property of the doped metal substrate on the base element. In one embodiment, the polymeric adhesive is in liquid state is and is an acrylic copolymer based adhesive.

In another aspect, the present invention provides a photocoat sheet. The sheet includes a base sheet. In one embodiment, the base sheet is a polymeric sheet. In another embodiment, the base sheet is a paper sheet. Further, the photocoat sheet includes a photocatalytic material coated on the base sheet. The photocoat material includes a doped metal oxide substrate capable of exhibiting photo catalytic behavior on being exposed to visible light. In one embodiment, the particle size of the doped metal oxide substrate ranges from about 18 nanometer (nm) to about 35 nm. Furthermore, the photocoat sheet includes a polymeric adhesive for improving the adhering property of the photocatalytic material on the base element.

This together with the other aspects of the present invention along with the various features of novelty that characterized the present disclosure is pointed out with particularity in claims annexed hereto and forms a part of the present invention. For better understanding of the present disclosure, its operating advantages, and the specified object attained by its uses, reference should be made to the accompanying descriptive matter in which there are illustrated exemplary embodiments of the present invention.

DESCRIPTION OF THE DRAWINGS

The features of the present invention will become better understood with reference to the following detailed description taken in conjunction with the accompanying drawing, in which:

FIG. 2 shows the anti-bacterial and anti-fungal property of the CFL lamp coated with the photocatalytic material as tested by IIT Kharagpur's testing lab, in accordance with an embodiment of the present invention; and FIG. 3 shows the air cleaning property of the CFL lamp coated with the photocatalytic material installed in a ladies toilet; and FIG. 4 shows the germ killing efficiency of the CFL lamp coated with the photocatalytic material as tested by International Testing Center, Panchkula, Haryana, India, in accordance with an embodiment of the present invention; FIG. 6 shows the germ killing efficiency of the photocoat sheet as used in an automobile.

DETAILED DESCRIPTION

Figure 1:
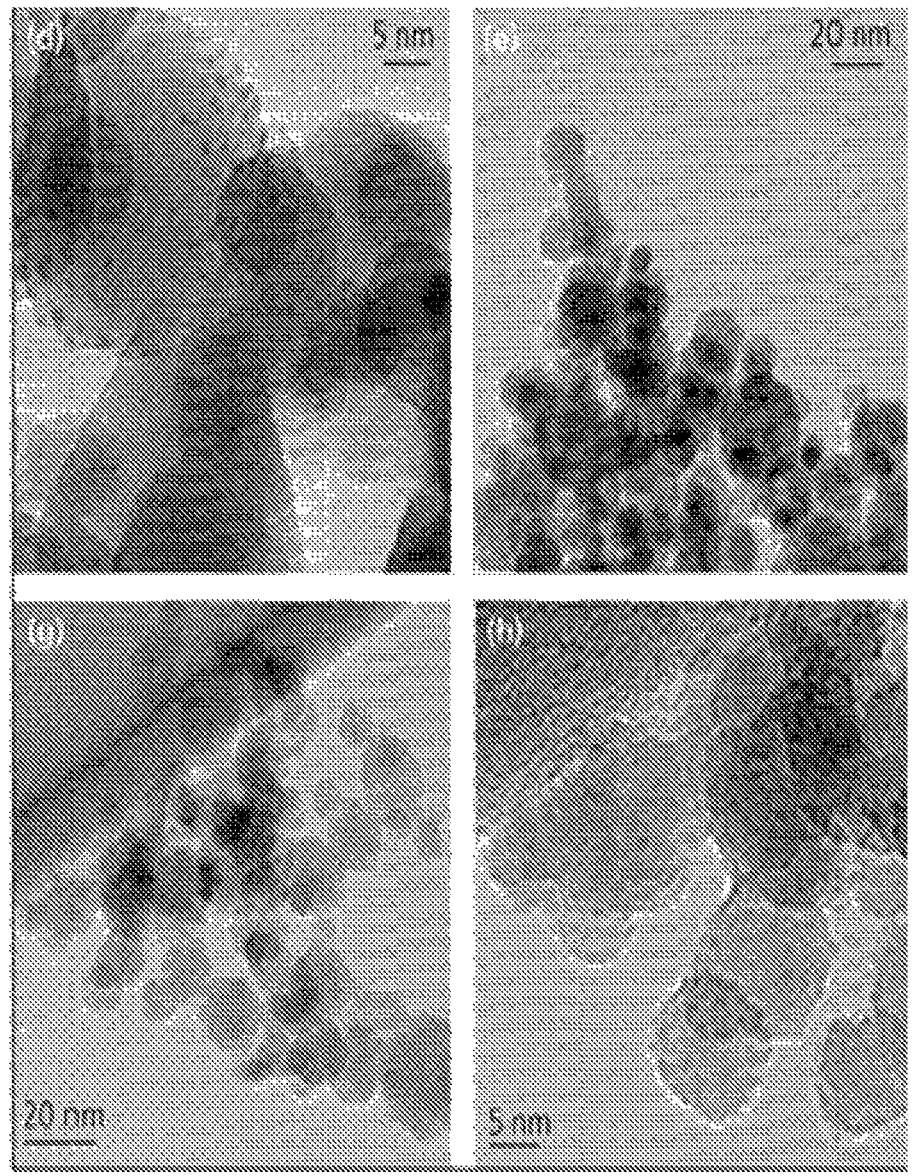
FIG. 1 illustrates nano particles of $TiO_2$ with different percentages of Platinum (Pt) doped in it, in accordance with an embodiment of the present invention.

For a thorough understanding of the present disclosure, reference is to be made to the following detailed description, including the appended claims. Although the present disclosure is described in connection with exemplary embodiments, the present invention is not intended to be limited to the specific forms set forth herein. It is understood that various omissions and substitutions of equivalents are contemplated as circumstances may suggest or render expedient, but these are intended to cover the application or implementation without departing from the spirit or scope of the claims of the present invention. Also, it is to be understood that the phraseology and terminology used herein is for the purpose of description and should not be regarded as limiting.

The terms "a" and "an" herein do not denote a limitation of quantity, but rather denote the presence of at least one of the referenced item.

The terms "having", "comprising", "including", and variations thereof signify the presence of a component.

The present invention relates to photocatalytic materials, and more particularly, to a novel photocatalytic material, process of developing the photocatalytic material, and various articles on which the materials may be applied. It should be understood to a person skilled in the art that the term photocatalytic material as mentioned herein refers to a composition that has the property of initiating molecular transformation or reactions at its surface. Such photocatalytic materials have various applications, especially in inducing molecular transformation of organic pollutants, thereby neutralizing them. More particularly, the photocatalytic materials oxidize the organic pollutants to neutralize them.

The present invention discloses a water soluble photocatalytic material capable of being adhered to an article by a conventional coating process. The water soluble nature of the photocatalytic material makes it easily applicable on various articles by conventional coating process, such as dip coating process. The composition of the photocatalytic material will now be described in details.

The photocatalytic material includes an active substrate that is the substrate which is capable of exhibiting photocatalytic behaviour. In one embodiment, the substrate is a doped metal oxide substrate. In one embodiment, the metal oxide is a transition metal oxide substrate.

In one embodiment, the metal oxide substrate is $TiO_2$ substrate. In another embodiment, the metal oxide substrate is $TiO_2$ substrate in anatase phase. It will be appreciated by those skilled in the art that the $TiO_2$ substrate has been known to have a property of initiating photocatalysis. This substrate is capable of exhibiting photocatalytic behaviour on being exposed to visible light, specifically light in ultra violet region. Such exposure produces causes the valence band electrons.

More specifically, the titania substrate when illuminated by UV radiation with a wavelength sufficient to displace electrons from the valence band of the catalyst; for titanium dioxide this is below 387.5 nm. An electron/hole pair is produced on the semiconductor surface. The photocatalytic oxidation of an organic species often proceeds via adsorption of the pollutant on the surface of the catalyst, followed by direct subtraction of the pollutant's electrons by positively charged holes.

In one embodiment, the $TiO_2$ substrate is doped $TiO_2$ substrate. It will be apparent to a person skilled in the art that the doping may be done to improve the photocatalytic activity of the substrate. More specifically, the doping allows the $TiO_2$ substrate to show enhanced activity even under visible light with wavelength greater than 400 nm, i.e., the doping inducing impurity in the band gap of the $TiO_2$ substrate, which leads to absorption in visible-light.

In one embodiment, the doping is done by at least one metallic element. In another embodiment, the doping is done by at least one non-metal. The suitable examples of metal dopants may include transition metal, such as Platinum (Pt), Boron and Cerium (B—Ce-codoped), Iron and Zinc, Silver, and the like. However, such examples of the metallic dopants should not be construed as a limitation of the present invention. In one embodiment of the present invention, the $TiO_2$ substrate is doped with Pt, which gives the best photocatalytic activity to the substrate.

The suitable examples of the non-metallic dopants may include, but are not limited to, Nitrogen, Carbon, Flourine, Iodine, and the like. In one embodiment of the present invention, the non-metallic dopant is Nitrogen.

The doped $TiO_2$ particles of the present invention have a specific size. The size of the doped $TiO_2$ substrate is in the range of 18 nanometer (nm) to about 35 nm. The particle size allows the substrate to show non toxic behavior which is a problem in conventional materials. In one embodiment, the $TiO_2$ substrate is in form of nano rods having particle size between 40 nm to 80 nm.

Such size of the nano particles provides a specific character to the photocatalytic material, by increasing the photocatalytic activity of the $TiO_2$ substrate manifold. Such increase of the photocatalytic activity is a direct result of the increased surface area of the $TiO_2$ particles in aforesaid particle range. However, it should be clearly understood that such particle range of the photocatalytic particles should not be construed as a limitation to the present invention.

The photocatalytic material of the present invention further includes a polymeric adhesive. The polymeric adhesive is provided for improving the adhering property of the water soluble photocatalytic material on various articles on which the photocatalytic material may be applied. The polymeric adhesive is preferably in liquid state. Suitable examples of the polymeric adhesive includes, but are not limited to, Polyurethanes, Acrylics, Acetates, such as Polyvinyl Acetates, Polychloroprenes, and the like. In one embodiment, the polymeric adhesive is Vinyl Acetate. However, it should be understood that such examples of the polymeric adhesives should not be construed as a limitation to the present invention, accordingly, any polymeric adhesive capable of forming a liquid phase with aforesaid metal oxide substrate, and especially, $TiO_2$ substrate, is equally applicable in the present invention.

In one embodiment, the polymeric adhesive is NORA® 485, which is a waterborne acrylic based adhesive supplied by Nora Systems GmbH. This adhesive is also available under the Trade Name and Synonyms as Nora 485 Acrylic Adhesive, and under Chemical Family of Acrylic copolymer dispersion. The adhesive essentially includes 60-64% of Acrylic copolymer, 35-39% of Calcium carbonate and <1% of Propylene glycol, has a pH of about 8.6, and a boiling point of 100° C.

The combination of the metal oxide, and specifically doped $TiO_2$ based substrate, and the polymeric adhesive as disclosed above, allows the photocatalytic material to exhibit high photocatalytic activity and proper adhesion to various articles by normal coating process, such as dip coating process.

In addition to the above, the photocatalytic material of the present invention may include various additional additives, and inorganic and organic binders to provide proper properties to the photocatalytic material. The binders are required to immobilize the photocatalytic material on various article surfaces. In one embodiment, the binders may be selected from a group consisting of epoxy based binders, silicate binders, phosphate binders, and combinations thereof. The additives may be added to impart one or more specific properties to the photocatalytic materials.

The photocatalytic material of the present invention will now be explained with the help of various examples.

Example 1—Pt Doped Photocatalytic Material

The process for producing the Pt doped photocatalytic material involves a characterization phase and a commercial production phase. The characterization phase is required to validate the particle size of the doped metallic oxide substrate, which in this case is doped $TiO_2$ substrate.

The characterization process initiates by adding 5 milliters (ml) of isopropoxide Ti(OC4(CH3)2)4-ethanol solution dropwise to 46 ml of distilled water. The purity of the isopropoxide taken is 99% Aldrich. The ratio of isopropoxide to water is therefore 5:46 volume by volume (v/v). Thereafter, the process involves adjusting the pH of the resultant mixture in a range of about 1.73 to 1.75. The pH adjusting may be done by adding 99.9% nitric acid to the mixture.

Once the pH is adjusted, the process includes stirring the mixture in a stirrer continuously for 24 hours. The stirring will result in appearance of blue translucent liquid. This translucent liquid is then evaporated in an evaporator at a temperature of about 40° C. to about 45° C. in a rotary evaporator. The resultant colloidal suspension so obtained is dried in a convention oven for 24 hours at a temperature of about 70° C. to about 75° C. The resultant powder is calcined at 400° C. for one hour to obtained the characterization sample, which is then characterized.

As mentioned above the size of the $TiO_2$ substrate is essential to the present invention. Therefore, the final powder obtained after calcination is then studied under an electron microscope, and the size is verified to be in the range of 18 nm to 35 nm. Once the characterization is successful, the process is commercially operated.

The commercial phase of the process for producing the water soluble photocatalytic material as disclosed above is designed to produce 10 liters of the photocatalytic material.

The process includes mixing 500 ml of Titanium Isopropoxide and ethanol solution with 4600 distilled water, wherein ratio of the solution to the distilled water is 5:46 by volume. Ideally, the Titanium Isoproxide solution is added to the water drop by drop. Thereafter, the process includes maintaining pH of the resultant mixture in the range of about 1.73 to about 1.75. The purity of the Titanium Isopropoxide taken is 99% Aldrich. The pH is maintained by adding 99.9% nitric acid to the mixture. The mixture is thereafter stirred for a prolonged period of time, in a stainlessted (316 C) tank or glass tank.

Once the mixture is stirred, the process further includes doping the mixture by adding a Platinum chloride (PtCl4) solution. More specifically, the process includes preparing a solution of PtCl4 into 4600 ml of distilled water, and adding the solution in the mixture. The mixture is thereafter stirred.

On conclusion of stirring, the process further includes evaporating about 75% to 80% of water by rotary evaporation (Light Brown Liquid). The resultant colloidal suspension in approximately 4000 ppm of $Pt—TiO_2$.

Once the Pt doped $TiO_2$ is produced, the process further includes preparing an adhesive solution and mixing the adhesive solution to the resultant colloidal suspension obtained.

The process therefore includes adding heated polymeric adhesive solution (50% v/v) to the resultant photocatalytic material. The polymeric adhesive solution is 50% v/v NORA 485 solution.

The process includes stirring continuously for prolonged period of time, and adding water to maintain a predetermined thickness of the photocatalytic material.

The mixture obtained, is the resultant photocatalytic material, which is water soluble, and is capable of being applied to various articles by various conventional process, such as dip coating process.

Example 2—Boron and Cerium Doped Photocatalytic Material

The $TiO_2$ based nanoparticle colloidal solutions (photocatalytic material) were prepared using the controlled hydrolysis of tetrabutyl titanate and titanous trichloride. In the process, a calculated amount of boric acid and cerous nitrate were dissolved in 50 ml of anhydrous ethanol. After 1 h of vigorous magnetic stirring, 2.5 ml of tetrabutyl titanate and 2.5 ml of titanous trichloride were added with vigorous magnetic stirring under anaerobic conditions (purged with N2). After the stirring, Sodium hydroxide solution (1 mol/l)

was then slowly added to the solution, surrounded by an ice bath. The clear solution was stirred at room temperature for 2 d. Subsequently, the gel that was formed was dried at 100° C. Finally, the prepared samples were calcined at desired temperatures (300, 500, 700, or 900° C.) for 5 hours.

After calcination, pure boron-doped and cerium-doped $TiO_2$ were prepared without adding boric acid and cerous nitrate under identical conditions, respectively. The prepared photocatalystic material were tested for its visible light activity and it was comparatively less when comparing with the Pt doped varieties. Also handling gaseous raw materials such as N was not practically easy and cost effective.

Example 3—Nitrogen Doped Photocatalytic Material

Next a photocatalytic material sample was prepared by Nitrogen doping. The Nitrogen doping in combination with a heterostructure of $TiO_2$ can not only modify the band structure of $TiO_2$ to make it more responsive to visible light, but also suppress charge recombination and lead $TiO_2$ to have enhanced photocatalytic activity. Also, one-dimensional $TiO_2$ nanostructures can serve as electron highways for efficient charge separation and, therefore, increase the lifetime of charge carriers and enhance the efficiency of interfacial charge transfer to the adsorbed substrate.

A simple one-pot synthetic strategy has been designed for preparing $TiO_2$ nanoparticles with good crystallinity, nitrogen doping and anatase/brookite binary structure characters, using $N_2H_4'H_2O$ as an in situ nitrogen doping source. The physicochemical properties of the catalysts can be tuned by simply changing the concentration ratios of $N_2H_4'H_2O$ to $TiO_2$ colloids. The synergistic effect of nitrogen doping in association with a one-dimensional and anatase/brookite binary structure is suggested to account for the higher catalytic activity of the $TiO_2$ nanorods for decomposing methyl orange and 4-chlorophenol compared to the nanoparticle counterparts under UV and/or visible light illumination.

Example 4—Iron and Zinc Doped Photocatalytic Material

For the $Fe^{3+}/Zn^{2+}$ co-doped $TiO_2$, $Fe(NO_3)_3\_9H_2O$ and $Zn(NO_3)_2\_6H_2O$ were mixed with the pure $TiO_2$ solution in a Fe:Zn molar ratio of 2:1. The final pH values of doped and undoped solutions were maintained at 0.85, which allows the gelation time of approximately 12 h for all samples. The resultant dispersion of colloidal particles defined as the sol, was then aged followed by gelation at room temperature for 48 h. The resulting sol-gel was heated at 100 8 C for 12 h to remove the residual solvents. The obtained amorphous $Fe^{3+}/Zn^{2+}$ co-doped $TiO_2$ particles were then impregnated in a 1 M$H_2SO_4$ solution for 1 h using 50 ml of solvent per gram of catalyst. The as-prepared sulfated and co-doped $TiO_2$ nanoparticles were then filtered and dried at 100 8 C for 3 h. These particles were slowly heated up to 145 8 C to surpass the exothermic reaction of $Ti(OBu)_4$ precursors. The sulfated particles were further filtered, dried, and calcined at 500 8 C under flowing air. In the degradation of phenol, a reduced activity of $TiO_2$ due to the codoped $Fe^{3+}/Zn^{2+}$-$TiO_2$ was observed under UV-vis light irradiation. However, a little enhancement with maximum degradation of 8.55% was noticed under visible light irradiation. The UV-vis photocatalytic activities of the sulfated and non-sulfated were found to be roughly the same. Though codoped, this reflects on the negative impact of some transition metal ions doping of $TiO_2$. Co-doping of $TiO_2$ was generally found to enhance the photocatalytic activity of the catalyst, though there are a few cases which are detrimental. The observation is quite true for any B codoped $TiO_2$. Boron has been found to contribute positively to the photocatalytic activity of $TiO_2$. The photocatalytic degradation of p-chlorophenol by N—F-codoped $TiO_2$ is better undertaken under UV light than under visible light irradiation. On the other hand, $Fe^{3+}$ and $Ho^{3+}$ co-doped $TiO_2$ in 21 min UV light irradiation for the degradation of MO does display some distinction over the undoped $TiO_2$, thus the material may not be considered a better photocatalyst than the Pt doped $TiO_2$.

Example 5—Silver Doped Photocatalytic Material

The method of preparing Ag-doped $TiO_2$ catalyst using ultrasonic assisted sol-gel for the same purpose with their respective modifications. In the process of preparation 30 ml titanium tetraisopropoxide is dissolved in 100 ml ethanol under vigorous stirring for about 15 min. Then distilled water and $HNO_3$ (5 ml, 0.1N) were added to complete the hydrolysis reaction in an ultrasonic bath. The amount of water varied between 15 ml and 36 ml, corresponding to hydrolysis ratios [H2O]/[TTIP] between 8 and 20. Then, a prepared $AgNO_3$ solution of 4 ml was added and the solutions were further homogenized for a few hours with a magnetic stirrer, and then aged at room temperature. On the other hand, dissolved 21 ml of $Ti(OBu)_4$ in 80 ml of absolute ethanol under stirring. The resulting solution was stirred in an ice bath; 2 ml of water and 0.2 ml of $HNO_3$ (50%) were added into another 80 ml of ethanol to make an ethanol-water-$HNO_3$ solution, which was slowly added to the $Ti(OBu)_4$-ethanol solution under stirring and cooling with ice.

When the resulting mixture turned to solution, the $AgNO_3$ solution was dripped into it; the dispersion was placed in a supersonic bath, stirred vigorously with a glass-stirring rod, and kept at 25.8° C. throughout the whole process. After sonification for 30 min, 1-2 ml of water was dripped into the dispersion at a rate of 0.5 ml/min until gel was formed. The gel was placed for 24 hours at room temperature and dried at 70° C. under vacuum condition, and then ground. The resulting powder was calcined at 500° C. for 4 hours for further studies.

Meanwhile, a pure $TiO_2$ sample was also prepared by the above procedure, but without addition of $AgNO_3$ solution. The prepared photo catalysts (Ag—$TiO_2$) were used for the photocatalytic degradation of bisphenol A (BPA). A great enhancement was noticed in the photocatalytic activity of the doped catalyst, especially at 1.0% Ag—$TiO_2$ when compared to the as-prepared $TiO_2$. This method appear to be better; it provided almost 100% degradation of BPA in 2 hours irradiation.

It will be apparent to a person skilled in the art that the aforesaid processes as described above including the quantities of various substances used are exemplary and should not be construed as a limitation to the present disclosure. Therefore, it is possible to obtain the same mixture with different volumes of the said components, and any such variation should not be construed to a limitation to the present disclosure. It is believed that the coating, as mentioned above, is obtained very effectively and inexpensively, and shows very high photocatalytic activity.

This photocatalytic active property of said water phase catalytic material helps in coating such material on various articles. Therefore, in another aspect, the present invention provides an air purifying article comprising a base element, and a photocatalytic material applied on the base element.

In one embodiment, the base element is a CFL lamp. It is envisaged, that the said coating is dip coated on an irradiating source, such as a CFL lamp, or a bulb, to obtained an air purifying lamp. This air purifying lamp has the property of being installed in homes, and providing as an effective de-odourizer, and pollutant eliminator. In another embodiment, the coating so obtained is applied on a surface of a wall to give de-odourizing property to the wall. Similarly, the said composition may be utilized for various other applications.

In another embodiment, the base element is selected from a group consisting of a wooden material, paper sheets, ceramic fiber nonwoven fabrics, glass material, and plastic resin materials. It is envisaged that the photocatalytic material is applied on Sticker papers. Alternatively, the photocatalytic material is mixed with general emulsion paint to convert general paint as an air purifying paint. It is also envisaged that the coating material may be applied to bathroom tiles and terra tiles, fabric based curtains and separators, and on wooden furniture.

Test Procedure and Test Results
Photocatalytic Material Coating on a CFL Lamp

The prospect of coating the photocatalytic material on a CFL lamp was explored as a means to extend the benefits to homes and hospices. Accordingly, next the CFL lamp has been tested for efficacy.

In one such study conducted by Indian Institute of Technology, Kharagpur, a CFL lamp coated with the photocatalytic material as defined in Example 1 (i.e., Pt doped sample) was provided to PK Sinha Cenre for Bioenergy at ITT, Kharagpur. The institute was instructed to test the lamp as an anti-microbial device.

The institute prepared test samples, which were yeast extract and a Potato Dextrose Agar (PDA). The composition of the yeast extract was as follows:
Yeast Extract—5 g/L
Dextrose Extract—10 g/L
Agar—2%
The composition of PDA was as follows:
PDA—39 g/L
Agar—2%

Using the above two extracts an appropriate media was prepared, sterilized (in autoclave at 121° C. at 15 psi for 15 min). Sterile media was poured on petri plates and left to solidify under laminar air flow conditions.

Next, two control plates, one of each medium type were prepared by exposing for two minutes in a CFL lamp unexposed room. These were then kept for incubation at 37° C. for 24 hours.

Two CFL lamp exposed plates, one of each medium type were prepared by exposing for two minutes in a CFL lamp exposed room and then kept for incubation at 37° C. for 24 hours.

Photographs were taken both after 12 hours and 24 hours of incubation time.

Results: After 12 hours incubation period, both the CFL lamp exposed plates showed no microbial growth while CFL unexposed plates showed both bacterial and fungal growth.

After 24 hours incubation time it was observed that the CFL lamp could effectively curb bacterial growth while fungal growth was curbed till considerable extent when compared to the control plates.

Therefore, the CFL lamp with the photocatalytic material in Example 1, exhibited a potent anti-bacterial effect while showing considerable anti-fungal effect. FIG. 2 provides the test result images showing the reduced bacterial and fungal activity as a result of the CFL lamp.

Next, the CFL lamp was tested in a real time rigorous environment. The lamp was installed in ladies toilet of Church gate station. After a continuous operation of the lamp, the air was tested. The results of the chemical and microbiological test analysis are shown in FIG. 3.

Another test was conducted to determine the efficacy of the CLF lamp coated with the photocatalytic material. This test was conducted by the International Testing Centre, Panchkula, Haryana, India and the purpose of the test was to determine the germ killing efficiency of the CLF lamp. The test was conducted on various bacterial and fungal cultures. The test parameter and the test results are provided in FIG. 4 of this specification.

Photocatalytic Material Coating on a Sheet Substrate

The prospect of coating the photo catalytic material on a sheet like substrate and/or film is conducted to determine the benefits of the photocatalytic coated sheets/films for the daily need of the users. The photocatalytic coated films are referred as photocoat sheet and these photocoat sheets are explored as a means to extend the hygienic benefits to the daily life of the users either inside the house or outside the house. Specifically, the efficacy and benefits of photocoat sheets is explored inside the vehicles.

The owner of vehicle or the passengers sitting in the vehicle usually does not give much attention towards the microbial hygiene as well as the examination of the indoor environment of the vehicle. Usually in metro cities, a person spends two to three hours of a day in travelling which includes the time spent either in going out for meetings or to purchase the domestic needs. During this time they are either in contact with the indoor environment of their personal vehicle or the public transport. The need for microbiological examination of vehicle indoor environment is felt because of repeated reports of dizziness, nausea, cough, diarrhea and many allergic symptoms felt by the travellers, these symptoms are an indication of presence of microbial contamination in the vicinity of the vehicle. Many of the corporate firms have an issue of high absenteeism in the staff members due to continuous health deterioration and discomfort. The majorly reported problems were nausea, dizziness, headache, flu, diarrhea and local skin allergies.

Figure 5:
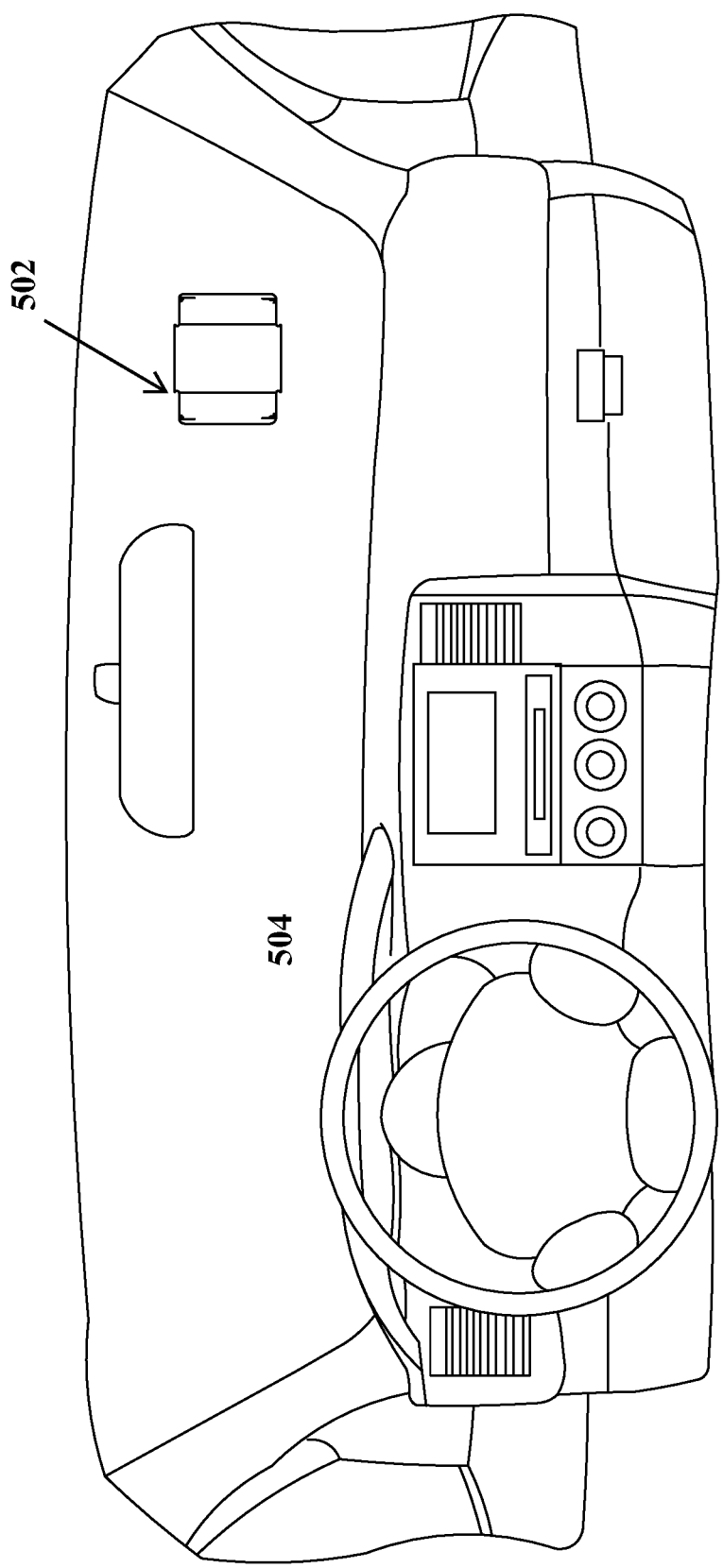
FIG. 5 shows the photocoat sheet mounted on the glass of an automobile.

To deal with the unhygienic conditions of the indoor environment of the vehicle a nano-engineered photocoat sheet are invented. This is shown in FIG. 5, where a photocoat sheet 502 is adhered to windscreen 504 of a vehicle. The photocoat sheet works as a sanitizer, anti-bacterial, purifier and de-odourizer and purifies the indoor air of the vehicle. The working principle of photocoat sheet imitates the natural process of photosynthesis, in which chlorophyll; a natural photo-catalyst converts carbon dioxide and water into oxygen and glucose in the presence of sunlight. It utilizes sunlight as the source of light for oxidative degradation of complex organic pollutants into simpler molecules like water and non-harmful gases. The working of this photocoat sheet does not require any artificial light source during day time but the working is not restricted to day time only as the photocoat sheet gets activated even in the presence of artificial light.

In an embodiment, the photocoat sheet of the present invention is made up of a base sheet having a photo catalytic material coated on the base sheet and a polymeric adhesive for improving the adhering property of the photocatalytic material on the base element. The photocatalytic material is a doped metal oxide substrate capable of exhibiting photo catalytic behavior on being exposed to visible light. The doped metal oxide substrate of the present invention is $TiO_2$ substrate doped with at least one metal selected from Platinum (Pt), Boron-Cerium, Iron-Zinc, and Silver. Wherein, the $TiO_2$ substrate is in its anatase phase.

In an embodiment, the particle size of the doped metal oxide substrate ranges from about 10 nanometer (nm) to about 45 nm. Preferably, the particle size of the doped metal oxide substrate ranges from about 18 nanometer (nm) to about 35 nm.

In an embodiment, the polymeric adhesive of the photo-coat sheet is an acrylic copolymer based adhesive and comprises an acrylic copolymer in an amount in the range of about 55 percent by weight to about 65 percent by weight, calcium carbonate in an amount in the range of about 25 percent by weight to about 40 percent by weight and propylene glycol in an amount in the range of about 2 percent by weight.

A study was conducted on various automobiles and the aim of the study was to quantify the air-borne and the surface-borne microbial loads in the automobiles during regular use and to rectify the health issues of the travellers by eradicating the microbial contaminants.

The automobiles used for staff transportation at a production plant are selected as the test vehicles i.e. bus, van, shift van and car. In each test, vehicle's areas are identified for surface sampling i.e. Front glass, Window glass, Head rest and the inside door handle. These areas are frequently touched during usage and they ensure that all parts of the vehicle are covered to assess the microbial load. The indoor air of the test vehicle is examined by Open plate air culture tests and to determine the microbial load on the surfaces wet swabs were taken from the dry surfaces.

Media Preparation:
SDA (Sabouraud Dextrose Agar): 6.5% SDA
6.5 gm of SDA was dissolved in 100 ml of DM water
Normal Saline (NS):
NaCl:—9.0 g per litter of DM water.
  A.) The SDA media was prepared and steam sterilized by standard autoclaving cycle (120° C. temp, 15 Lbps pressure for 20 mins).
  B.) The pre-sterilized Petri plates were filled with the sterile SDA media in the laminar air flow unit.
  C.) These petri-plates were left in the laminar air flow unit for 25 min to let the media settle in the plates.

I. To Determine the Initial Microbial Load in the Test Vehicle:
  i. Samples were taken on the zero hour time from front glass, rear window glass, head rest and door handles in the vehicles.
  ii. Open plate air tests were done in the vehicles under test.
  iii. These samples were then inoculated on the media plates and incubated at 37° C. for time period of 24 hours.

II. Application of Photocatalytic Film in the Test Vehicles:
The photocatalytic film was applied on the front glass, window glass and the rear glass in the vehicles.

It was also considered that while applying the photocatalytic film it was ensured that no air gaps were trapped under the film.

III. To Determine the Microbial Load After Photocatalytic Film Application:
1.) Surface samples were taken at an interval of 20 h, 23 h, 26 h and 44 h from front glass, window glass, head rest and door handle.
2.) These samples were then inoculated on SDA media in the petri plates and were incubated at 37° C. for 24 hours.

3.) Open plate air culture tests were also done after 20 hour, 23 hour, 26 hour and 44 hour of the photocatalytic film application in all the vehicles under test.
4.) The resulting plates were analyzed for colony forming unit (CFU) count and the results were photographed.

Observations:
The results of the chemical and microbiological test analysis are shown in FIG. 6 of the specification.

The advantages of the above mentioned photocatalytic materials and articles obtained by the coatings are many. Firstly, the materials are water soluble, thereby making them easily applicable on various articles. Secondly, the materials have high rate of de-odourizing and purifying its surroundings. Thirdly, the materials can be easily activated by irradiating with visible light. Fourthly, materials so obtained herein offer a means of absorbing ultra violet light from the visible light spectrum, thereby neutralizing the bad effects of ultra violet light. In addition, the materials are easy to obtain, durable and inexpensive to manufacture. In fact, most of the substances used are inexpensive and easily obtainable in the surroundings. Lastly, the materials obtained are easily usable by mankind. For example, the Photocatalytic sheet so obtained by coating the photocatalytic material can be easily installed in a vehicle and may provide as a source of absorption of UV radiation and cleaning the indoor environment of the vehicle. Moreover, the materials are non-toxic in nature and non polluting to the environment.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

I claim:
1. A water soluble photocatalytic material capable of being adhered to an article by a coating process, the water soluble photocatalytic material comprising:
  a) a doped $TiO_2$ substrate capable of exhibiting photocatalytic behavior on being exposed to visible light, the doped $TiO_2$ substrate being in a form of $TiO_2$ nano rods; and
  b) a polymeric adhesive that enhances an adhering property of the water soluble photocatalytic material capable of being adhered to the article, wherein the polymeric adhesive comprises:
    an acrylic copolymer added in an amount in a range of about 55 percent by weight to about 65 percent by weight,
    calcium carbonate added in an amount in a range of about 25 percent by weight to about 40 percent by weight, and
    propylene glycol added in an amount less than about 2 percent by weight.

2. The photocatalytic material as claimed in claim 1, wherein the $TiO_2$ is doped with at least one metal.

3. The photocatalytic material as claimed in claim 2, wherein the metal dopant is Platinum (Pt).

4. The photocatalytic material as claimed in claim 2, wherein the dopant is at least one selected from the group consisting of Boron-Cerium, Iron-Zinc, and Silver.

5. The photocatalytic material as claimed in claim 1, wherein the $TiO_2$ is doped with Nitrogen.

6. The photocatalytic material as claimed in claim 1, wherein the $TiO_2$ substrate is in anatase phase.

7. The photocatalytic material as claimed in claim 1, wherein the polymeric adhesive is a water soluble liquid phase adhesive.

8. The photocatalytic material as claimed in claim 1, wherein the dopant is Nitrogen (N).

9. The photocatalytic material as claimed in claim 1, wherein the $TiO_2$ nano rods have a particle size in a range of 40 nanometers to 80 nanometers.

10. An air purifying article comprising:
a base element; and
a photocatalytic material comprising:
a doped $TiO_2$ substrate capable of exhibiting photo catalytic behavior on being exposed to visible light, the doped $TiO_2$ substrate being in a form of $TiO_2$ nano rods, and
a polymeric adhesive that enhances an adhering property of the photocatalytic material capable of being adhered to the base element, wherein the polymeric adhesive comprises:
an acrylic copolymer added in an amount in range of about 55 percent by weight to about 65 percent by weight,
calcium carbonate added in an amount in a range of about 25 percent by weight to about 40 percent by weight, and
propylene glycol added in an amount less than about 2 percent by weight.

11. The air purifying article as claimed in claim 10, wherein the base element is a CFL lamp.

12. The air purifying article as claimed in claim 10, wherein the base element comprises a member selected from the group consisting of a wooden material, a paper sheet, a polymer sheet, a ceramic fiber nonwoven fabric, and a plastic resin material.

13. The air purifying article as claimed in claim 10, wherein the $TiO_2$ is doped with Platinum (Pt).

14. The air purifying article as claimed in claim 10, wherein the $TiO_2$ substrate is in anatase phase.

15. The air purifying article as claimed in claim 10, wherein the polymeric adhesive is a water soluble liquid phase adhesive.

16. The air purifying article as claimed in claim 10, wherein the $TiO_2$ nano rods have a particle size in a range of 40 nanometers to 80 nanometers.

17. A photocoat sheet comprising:
a base sheet; and
a photocatalytic material coated on the base sheet, the photocatalytic material comprising:
a doped $TiO_2$ substrate capable of exhibiting photo catalytic behavior on being exposed to visible light, the doped $TiO_2$ substrate being in a form of $TiO_2$ nano rods, and
a polymeric adhesive that enhances an adhering property of the photocatalytic material capable of being adhered to the base sheet, wherein the polymeric adhesive comprises:
an acrylic copolymer added in an amount in a range of about 55 percent by weight to about 65 percent by weight,
calcium carbonate added in an amount in a range of about 25 percent by weight to about 40 percent by weight, and
propylene glycol added in an amount less than about 2 percent by weight.

18. The photocoat sheet as claimed in claim 17, wherein the $TiO_2$ substrate is in anatase phase.

19. The photocoat sheet as claimed in claim 17, wherein the $TiO_2$ is doped with at least one metal.

20. The photocoat sheet as claimed in claim 19, wherein the metal dopant is Platinum (Pt).

21. The photocoat sheet as claimed in claim 19, wherein the dopant is at least one selected from the group consisting of Boron-Cerium, Iron-Zinc, and Silver.

22. The photocoat sheet as claimed in claim 17, wherein the $TiO_2$ is doped with Nitrogen.

23. The photocoat sheet as claimed in claim 17, wherein the $TiO_2$ nano rods have a particle size in a range of 40 nanometers to 80 nanometers.

* * * * *